United States Patent [19]

McLafferty et al.

[11] 3,997,298
[45] Dec. 14, 1976

[54] LIQUID CHROMATOGRAPHY-MASS SPECTROMETRY SYSTEM AND METHOD

[75] Inventors: Fred W. McLafferty, Ithaca, N.Y.; Michael A. Baldwin, Carshalton Beeches, England

[73] Assignee: Cornell Research Foundation, Inc., Ithaca, N.Y.

[22] Filed: Feb. 27, 1975

[21] Appl. No.: 553,519

[52] U.S. Cl. .......................... 23/253 R; 23/230 R; 73/61.1 C; 210/198 C
[51] Int. Cl.[2] ....................................... G01N 31/08
[58] Field of Search ............ 23/230 R, 253 R, 259; 73/66.1 C; 210/198 C; 250/281

[56] References Cited

UNITED STATES PATENTS 3,292,420  12/1968  Scott .............................. 23/230 X
3,718,432  2/1973  Roth ................................ 23/230 R

OTHER PUBLICATIONS

Karasek et al., "Separation and Identification of Multi-component Mixtures Using Centri-Chromatography/Mass Spectrometry," Anal. Chem. vol. 44, No. 8, (July 1972), pp. 1488-1490.

Primary Examiner—R.E. Serwin
Attorney, Agent, or Firm—Lawrence E. Laubscher; Theodore C. Wood; Ralph R. Barnard

[57] ABSTRACT

Liquid chromatography-mass spectrometer apparatus and method are disclosed for analyzing the components of a complex mixture, characterized in that at least a portion of the eluted effluent from the liquid column is continuously introduced directly into the ionization chamber of a chemical ionization mass spectrometer for detection of the eluted sample components. Use is made of restricted capillary tube means for introducing the complex mixture directly into the chemical ionization ion source chamber, and diffusion pump and cryogenic pump means for obtaining the desired vacuum in the ion source chamber. The solvent is used as the agent necessary for chemical ionization, thereby making it unnecessary to remove all of the solvent before introducing the sample into the analyzer. Mass spectra is taken either on a repetitive basis, or the instrument is operable to monitor the total abundance of peaks other than those resulting from the solvent.

5 Claims, 8 Drawing Figures

LIQUID CHROMATOGRAPHY-MASS SPECTROMETRY SYSTEM AND METHOD

DESCRIPTION OF THE PRIOR ART

Liquid chromatography techniques for analyzing complex mixtures are well known in the patented prior art, as evidenced by the U.S. Pat. to Bakalyar et al. No. 3,446,057, Skeggs No. 3,230,048, and Waters Nos. 3,522,725 and 3,537,585, and the use of mass spectrometers in gas analyzing systems has been proposed in the patents to Llewellyn et al. U.S. Pat. No. 3,429,105, Haruki et al. U.S. Pat. No. 3,581,465, Saunders U.S. Pat. No. 3,662,520 and Grunnee et al. U.S. Pat. No. 3,678,656, among others.

It has also been proposed to analyze complex mixtures in a strictly batch-wise manner. A certain volume of the liquid chromatography effluent is collected, the solvent is evaporated off, and the residue is introduced into the mass spectrometer. R. E. Lovins, S. R. Ellis, G. D. Talbert and C. R. McKinney, *Anal. Chem.*, 45, 1553 (1973). Such a technique has the drawback that it cannot supply a chromatographic curve showing peak shapes and other valuable indications of column performance, and also causes the mixing of components which elute closer together than the sampling points. Furthermore, direct sampling of pure organic liquids into a conventional electron ionization mass spectrometer has been reported. V. L. Tal'Rose, V. D. Grishen, V. E. Skurat and G. D. Tantsyrev, "Recent Developments in Mass Spectrometry," K. Ogata and T. Hayakawa, eds., University Park Press, Baltimore, 1970, p. 1218. The very low source pressure required limits the liquid flow rates to less than $10^{-6}$ ml/minute, whereby practical sensitivities for solutes cannot be obtained.

Liquid chromatography has experienced an explosive growth in analytical applications reminiscent of that shown by gas chromatography a decade or more ago. One of the most serious instrumental problems limiting further applications is the availability of detector systems of suitable sensitivity and specificity. The two main general purpose detectors which are now used for liquid chromatography columns are the differential refractometer (DR) and ultraviolet spectrophotometer (UV). A differential refractometer can detect most compounds but with sensitivities of only about $10^{-7}$ grams. It cannot be used for gradient elution. Ultraviolet detection can give sensitivites of $10^{-9}$ grams in favorable cases, but will not detect many materials. The present invention was developed to provide sensitivities which are at least comparable (and preferably greater) than UV for all compounds with sufficient vapor pressure and thermal stability. A further advantage is the fact that the mass spectral information is much more valuable for determination of the identify and structure of the eluted component than either DR or UV.

SUMMARY OF THE INVENTION

In accordance with the present invention, liquid chromatography apparatus is provided for which eluted sample components are detected by continuous direct introduction of the solutions into a chemical ionization mass spectrometer coupled to a laboratory minicomputer (COM). The resulting liquid chromatography system shows many advantages now well established for gas chromatography-mass spectrometer-computer systems, such as the real time preparation of reconstructed liquid chromatograms, mass chromatograms, and multiple ion detection. Detection specificities made possible by the individual mass peaks are superior, and the subnanogram detection sensitivities achieved are at least comparable to those of any other detector, and are applicable to most samples meeting the low vapor pressure requirements of direct chemical ionization.

Thus, the solution emerging from the liquid chromatography column can be introduced continuously into the ionization chamber of the chemical ionization mass spectrometer. Mass spectra can be taken on a repetitive basis, or the instrument set up to monitor the total abundance of peaks other than those resulting from the solvent. In this fashion, whenever a solute appears in the chromatographic effluent, ions from it should produce a signal indicative of the concentration of the solute in the effluent. The total amount of solvent permitted which can be introduced into the mass spectrometer is determined by the pumping speed of the instrument. If this is insufficient, a preconcentration of the sample will be valuable. One way in which we have achieved this is to allow the solution to drop through an evacuated chamber into a sample cup connected to the mass spectrometer. The more volatile solvent evaporates preferentially in the evacuated chamber, thus concentrating the solution and reducing the volume per minute which must be accepted by the mass spectrometer. By using the solvent as part or all of the "reagent gas" necessary for chemical ionization, it becomes unnecessary to remove all of the solvent before introducing the sample into the analyzer.

Accordingly, a primary object of the present invention is to provide an improved liquid chromatography method and apparatus for analyzing the components of a complex mixture, characterized in that at least a portion of the eluted effluent from the liquid column is introduced continuously and directly into the ion source chamber of a chemical ionization mass spectrometer connected with a computer. In one embodiment, interface means are provided for introducing a portion of the effluent continuously into the ion source chamber at a desired flow rate which is appreciably lower (approximately 1%) than that of the flow rate of the solution in the liquid column. Thus, for a flow rate in a conventional liquid column of 0.5 - 1.5 ml/minute, a continuous flow rate of 10–12 $\mu$l/minute to the ion source chamber is achieved by the use of restricted capillary tube means. In an alternate embodiment using a micro liquid column (requiring only about 0.01 ml/minute solvent flow rate, for example) the total liquid column effluent is supplied continuously to the chemical ionization mass spectrometer.

In accordance with a more specific object of the invention, capillary tube means having a restriction in the ion source chamber are provided for continuously introducing a liquid stream directly into the source of the chemical ionization mass spectrometer. This interface is used to integrate a commercial liquid chromatograph and a chemical ionization mass spectrometer with both manual and automated data collection.

A further object of the invention is to provide apparatus of the type described above wherein gas evacuation of the ion source chamber of the chemical ionization mass spectrometer is effected by means of a diffusion pump and a cryogenic pump. The diffusion pump pumps 500 l/second of air at the source entrance because of pipe conductance, and the cryotrap, which is chilled by liquid nitrogen and is located immediately above the source, is especially helpful for higher molecular weight solvents. The solvent used in the liquid chromatography separation must have a lower proton affinity than the solute or the sensitivity of the method will be sharply reduced. Fortunately, the common solvents used in liquid chromatography, such as water and hexane have unusually low proton affinities.

DESCRIPTION OF THE DRAWINGS

Other objects and advantages of the invention will become apparent from a study of the following specification when viewed in the light of the accompanying drawing, in which.

Figure 1:
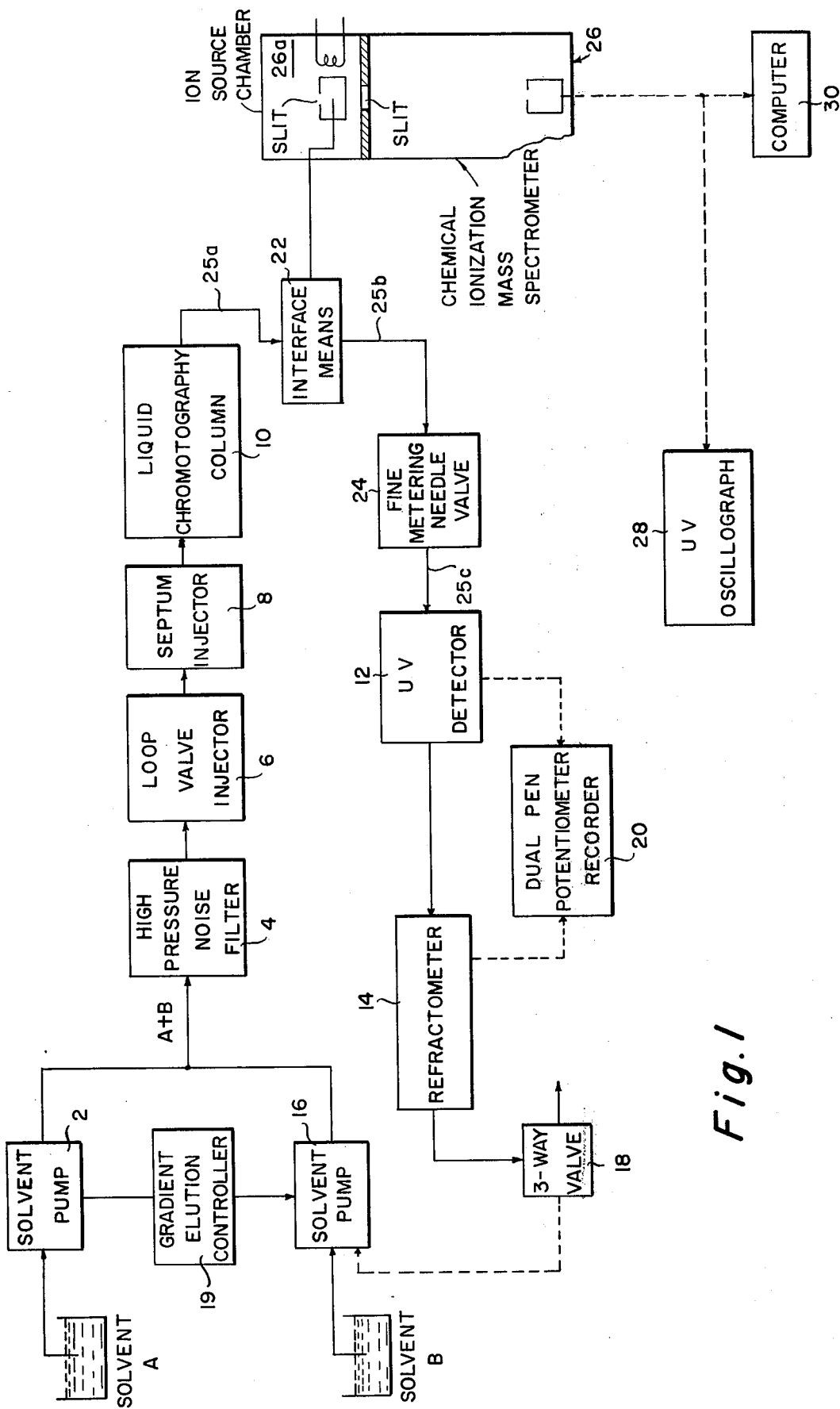
FIG. 1 is a block diagram of the liquid chromatography-mass spectrometry system in accordance with the present invention.

Referring now more particularly to FIG. 1 of the drawing, the liquid chromatography-mass spectrometry system of the present invention includes a conventional chromatograph apparatus (such as the ALC 202 unit of Waters Associates) including a first solvent pump 2, high pressure noise filter 4, valve loop injector 6, septum injector 8, liquid chromatography column 10, ultra violet detector 12, and refractometer detector 14. Also provided is a second solvent pump 16 (such as a M-6000 pump) connected with the refractometer output via three-way valve 18, and a conventional gradient elution controller 19. Dual pen potentiometric recorder 20 is connected with the UV detector 12 and the refractometer in a conventional manner.

In accordance with the present invention, capillary splitter interface means 22 and a fine metering needle valve 24 are connected by conduit 25 between the output of the liquid chromatography column and the UV detector for diverting a small portion (about 1%) of the eluted effluent from the column to the ion source chamber 26a of a chemical ionization mass spectrometer 26. A fine mesh filter, not shown, is provided at the entrance of the interface means 22 which eliminates most capillary plugging problems except for unusually high solute concentrations. As will be described in greater detail below, the system is designed to cause solutions to enter continuously into the chemical ionization ion source at a rate of approximately 1% of the normal rate of the liquid column effluent, making possible the detection of a wide variety of compounds at concentrations in the total effluent far below those now possible with refractometer index or ultraviolet detection. More particularly, in one embodiment of the invention, the solution had a flow rate of 0.5–1.5 ml/minute in the liquid column, and a continuous 10–12 μl/minute flow rate in the interface. The chemical ionization mass spectrometer is of conventional construction (such as a Hitachi RMH-2, 5400 volt ion acceleration, 500 eV ionizing electrons mass spectrometer modified for chemical ionization). The electrical output from the mass spectrometer 26 is connected with an ultraviolet oscillograph 28 and a laboratory on-line minicomputer 30 (such as the PDP 11/45 computer manufactured by Digital Equipment Corporation, Maynard, Mass., using software similar to previously described algorithms for gas chromatography-mass spectrometer processing of data using a cyclic scanning mode).

Figure 2:
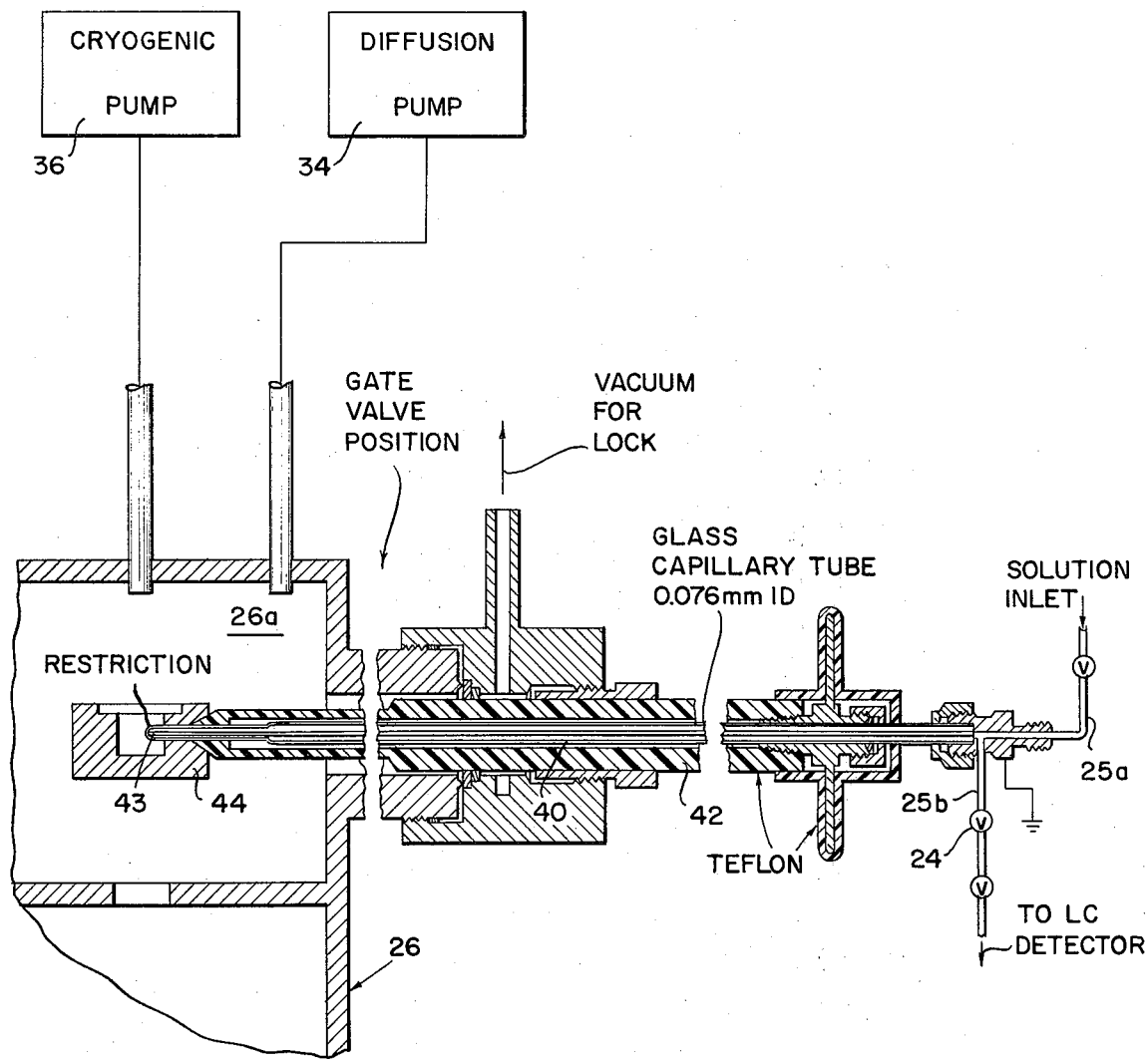
FIGS. 2 and 3 are detailed sectional and exploded perspective views, respectively, of the inlet probe means for continuously introducing solutions into the ionization chamber of the chemical ionization mass spectrometer.

Referring now to FIG. 2, gas evacuation of ion source chamber 26a is effected by diffusion pump 34 and cryogenic pump 36. The diffusion pump (which may be a VHS-6 pump produced by Varian having a capacity of 2500 l/second) pumps 500 l/second of air at the source entrance because of pipe conductance. The cryotrap is a cold finger of 2 inches outer diameter whose active surface has been doubled by milling, and is chilled by liquid nitrogen. It is located immediately above the source. The cryogenic pump is especially helpful for higher molecular weight solvents, increasing the pumping speed by approximately 70% for a solvent such as acetonitrile. With the help of the two pumps, 12 μl/min of liquid acetonitrile introduced through the interface gives a source pressure of 1 × 10⁻⁴ torr in the source housing, and 10⁻⁶ torr in the analyzer which is isolated from the source by a small differentially-pumped slit. With this system chromatographic runs of as long as 6 hours have been made without changing the operating conditions. Regeneration of the cold trap is done overnight.

Figure 3:
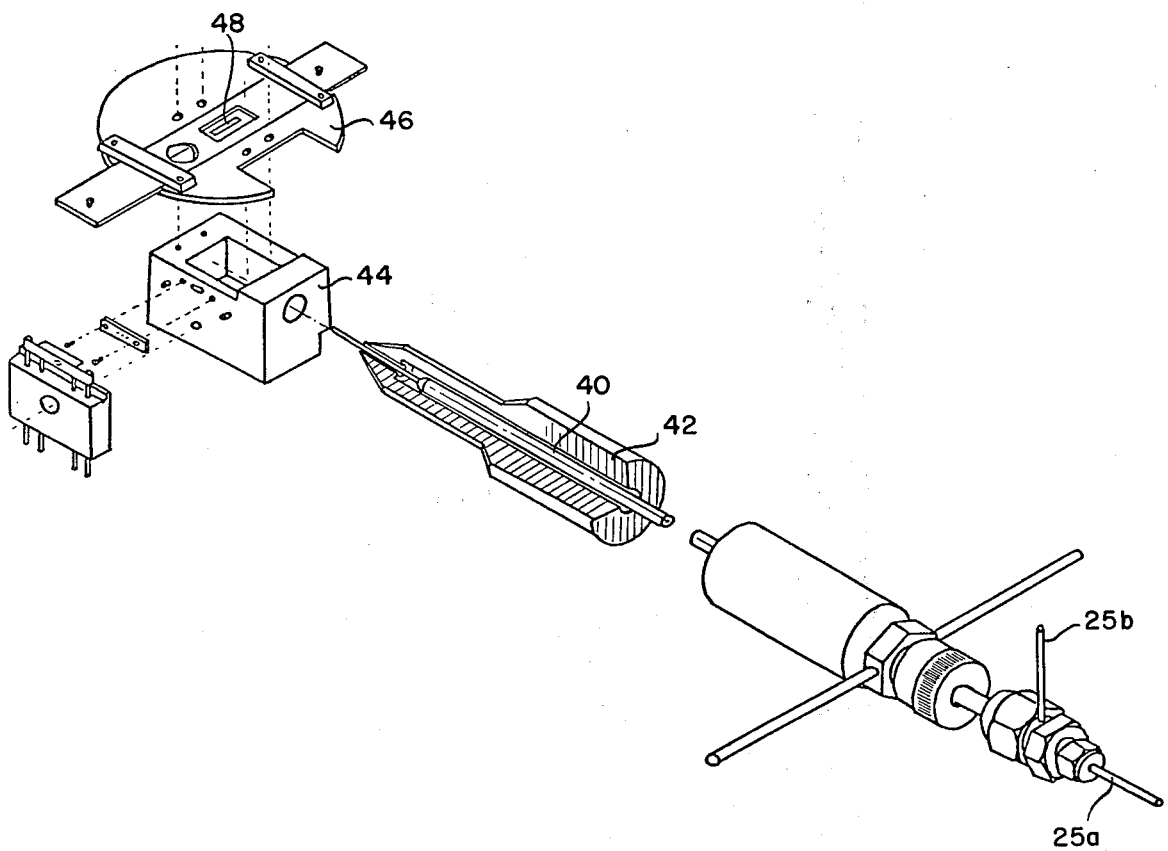

As shown in FIGS. 2 and 3, the interface means includes a glass capillary tube 40 of 0.076 mm internal diameter which passes through the center of teflon rod 42. This rod is inserted through the vacuum lock made for the direct solids introduction probe to provide a vacuum tight seal to the ion source. Excess glass at the ion source end of the capillary tube is conveniently removed and a suitable flow restriction 43 is formed by drawing out the tip in a small flame. Delay time in the capillary is 6 seconds at a flow rate of 0.01 ml/min; this rate can be readily maintained for times typical of those required for liquid column runs. Flows of several times this rate can be achieved, but the possibility of high voltage breakdown in the source is increased. Current flow through the capillary using pure methanol is <1 μ amp at an ion source potential of 9600 V. For solutions of much higher conductivity, dangerous conductance through the capillary could be avoided by using a quadrupole or other spectrometer with a low ion source potential.

The ion source block 44 is provided with a cover 46 (FIG. 3) which contains a relatively large slit 48 (preferably, about 0.5 mm by 8 mm). This lowers the ion source pressure and yields less high molecular weight solvent clusters. It also gives a more intense ion beam, thus increasing the overall sensitivity of the system. The actual ion source pressure is not known; at the tip of the inlet capillary it corresponds to the vapor pressure of the solvent at the source temperature (222° C), and decreases through the ion source and ion exit slit down to $10^{-4}$ torr in the ion source housing. Thus there is some effect of capillary tip position relative to the path of the high energy electrons (500 eV) and the chemical ionization spectral data. The system design leads to a very high pressure gradient in the ion source, so that the source pressure is adjusted to give reasonably low amounts of the telomerized solvent ions. The capillary tube restriction 43, which is on the order of one micron and is arranged in the ion source, permits the desired continuous introduction of the liquid column effluent into the ion source.

OPERATION

The mass spectrum depends on the nature of the solvent-solute couple, but with all the examples studied, a mass spectrum indicative of the solute was obtained. In general, polar solvents such as tetrahydrofuran, acetonitrile, methanol and water produce simple mass spectra where $(M + H)^+$ is the abundant if not the only detected ion. Saturated hydrocarbon solvents such as n-pentane give abundant hydride abstraction products, $(M - H)^+$.

Figure 4:
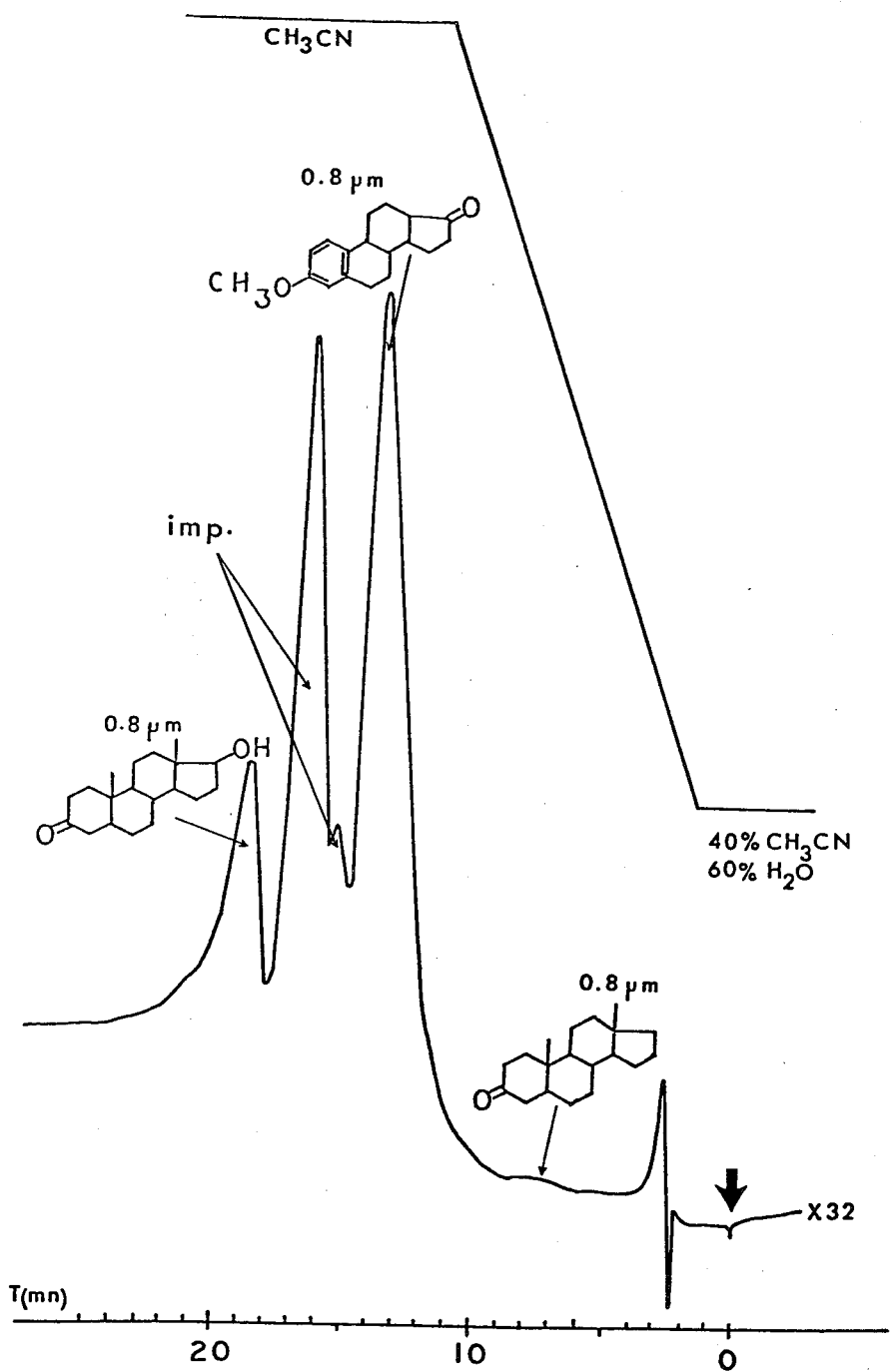
FIG. 4 is a graph illustrating the chemical ionization mass spectra of 11-keto, tricontanic acid methyl ester in chloroform.

Chloroform, a solvent often used in adsorption liquid chromatography, is attractive for liquid chromatography-mass spectrometry because useful fragmentations are often induced in the solute molecule. The mass spectra of the long chain keto-ester shown in FIG. 4 exhibits informative peaks such as $(M - 1 - 32)^+$ and $(M + 1 - 18 - 32)^+$ when run in chloroform (chromatography on a 2 foot column packed with Corasil 2); however, only the $(M + H)^+$ peak is observed when the same sample is run in tetrahydrofuran, acetonitrile, methanol, or mixtures of these solvents. Chloroform gives mainly $CHCl_2^+$ and $CCl_3^+$ as solvent peaks, with peaks such as $(M - H)^+$, $(M + H)^+$, $(M + Cl)^+$, and $(M + CHCl_2)^+$ indicating the solute molecule.

Regarding reverse phase liquid chromatography, preliminary results indicate that solute fragmentation can be induced by addition of other ionizing reagent gases. Of special applicability for liquid chromatography-mass spectometry is gradient elution chromatography on reverse phase bonded packing. Such columns do not bleed and do not need regeneration after use, a major limitation in gradient adsorption liquid chromatography.

Figure 5:
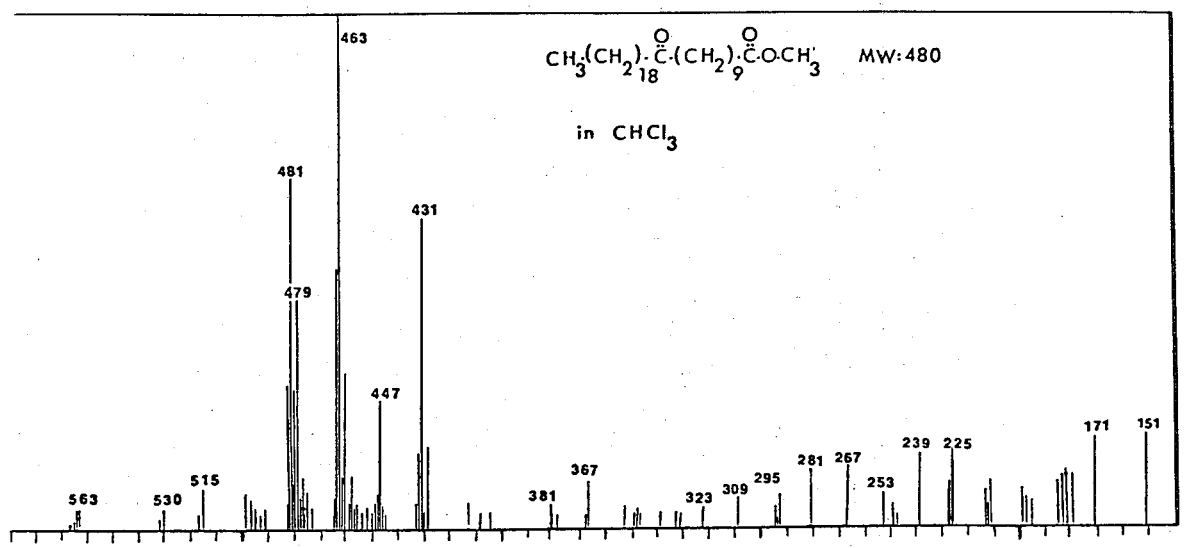
FIG. 5 is a representation of a liquid column chromatogram for steroid analysis from the UV detector response.
Figure 6:
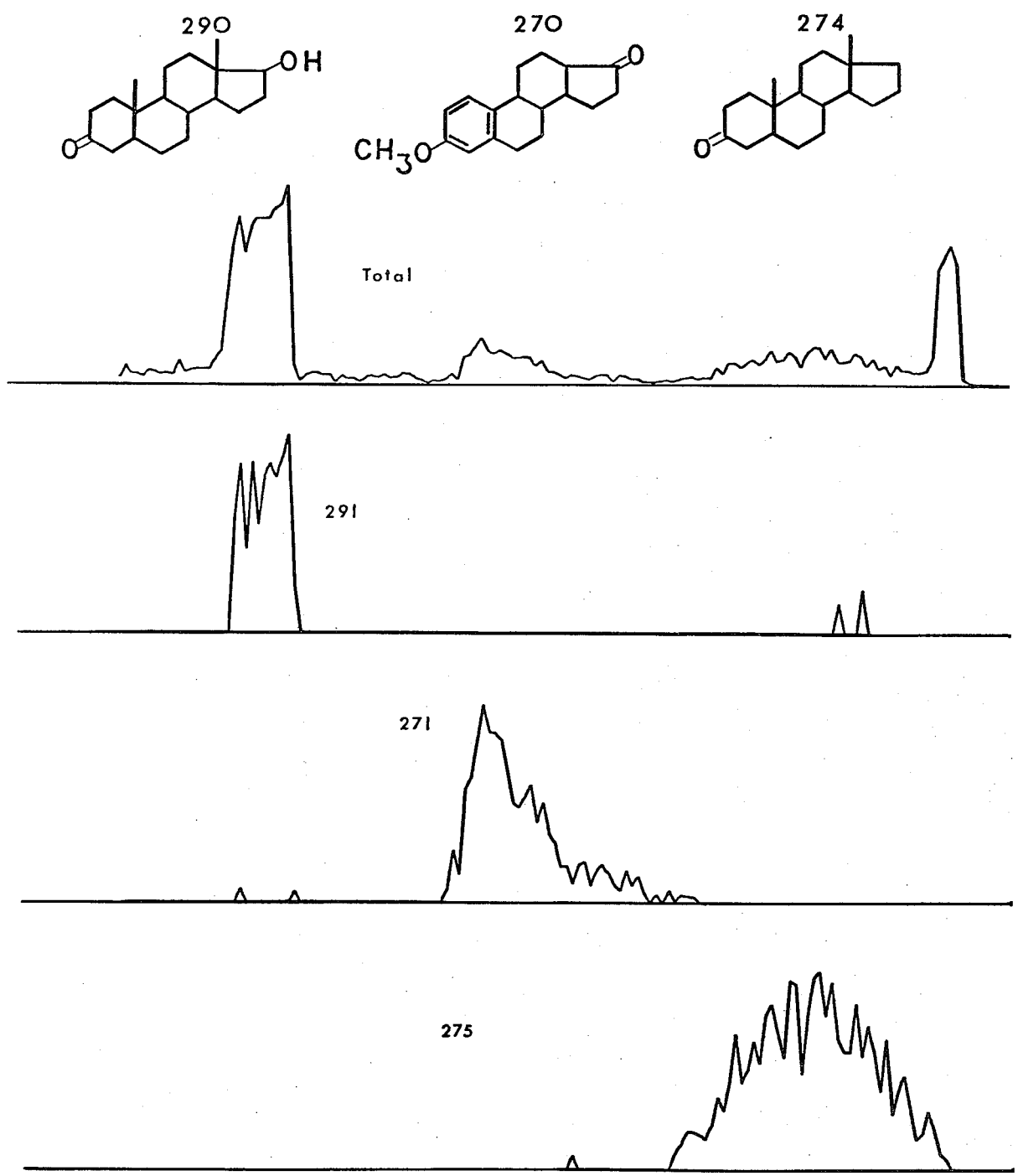
FIG. 6 is a representation of total and mass chromatograms of the quasi-molecular ions retrieved from the computer for steroid analysis.

As an example, the liquid chromatography analysis of three steroids on a $C_{18}$-Corasil 2, 2 foot column, was monitored by the UV detector (FIG. 5), and independently recorded and processed by the mass spectrometer computer system (FIG. 6). The refractive index detector cannot be used here because its response is greatly affected by changes in the solvent composition.

A mixture of 5-α-3 androstanone, estrone methyl ether and androstanolone was dissolved in tetrahydrofuran. Injection of 10 μl introduced 0.8 μmole of each sample on column. A linear gradient from 40% $CH_3CN$-60% $H_2O$ to pure acetonitrile at 1 ml/min was run in 10 min. The mass spectrometer was run at resolution 1500, source temperature 200° C, ionizing electron energy 500 eV, and emission current 0.7 mA. Repetitive cyclic scan speed was 10 sec/decade from mass 600 to mass 120, with a flyback time of 2 sec. The source housing pressure fluctuated somewhat because pumping speed and vaporization rate is solvent dependent, but it remained between $0.8 \times 10^{-5}$ torr and $1.5 \times 10^{-4}$ torr.

The androstanone gave no appreciable liquid chromatographic peak using the UV detector. However an abundant peak seen by the UV was not detected by the mass spectrometer; this was not due to one of the originally introduced samples, but apparently to an impurity producing no appreciable peaks above m/e 120. The presence of such impurities could be misleading in peak assignment if the UV had been the only used detector. The tetrahydrofuran used for dissolution and injection of the samples gave ions at m/e 143 (2 THF−H)$^+$ and 145 (2 THF + H)$^+$, so that it also produces a response in the total mass spectrometer ion current soon after injection. The mass spectrometer correctly detected the three samples, the solvent, but nothing else. Mass chromatograms of single ions characteristic of each sample allowed correct identifications of each liquid chromatography peak (FIG. 6).

Basic system sensitivity depends on the solvent and the solute. However, 1 μg of cholesterol injected on column in acetonitrile gave a spectrum (10 sec/decade) which exhibited a 369 peak with S/N = 5 (chemical ionization of cholesterol in methanol, tetrahydrofuran, and acetonitrile exhibits the $(M + H - H_2O)^+$ as base peak). A chromatogram of 200 ng of tert-butylanthraquinone with the mass spectrometer tuned so that only mass 265, $(M + H)^+$, would reach the detector (single ion detection) gave a peak with a S/N>4 while giving a peak of 30 sec baseline width on the UV.

It does not appear that the described system can perform all the various forms of modern liquid chromatography. It is not suited for ion exchange chromatography because the salts used in the buffered mobile phase would plug the capillary, precipitate in the ion source, and allow dangerous electric discharge from the course high voltage through the conductive liquid. Size separation chromatography is not possible either because high weight molecules with no vapor pressure cannot be mass analyzed. Liquid-liquid chromatography in which liquid stationary phases are always present in the mobile solvent might give interfering background in the mass spectrometer.

The continuous monitoring of a liquid chromatograph with only a mass spectrometer is feasible on a routine basis. The mass spectrum provides directly molecular weight information on the eluted solutes, and it appears that the addition of a proper reagent gas will also provide fragment ion structure information. The invention is applicable to polypeptide sequencing through hydrolysis, liquid chromatography separation, and on-line mass spectral sequencing of the non-derivatized oligopeptides. Coupling the liquid chromagraph with a chemical ionization mass spectrometer is simple; the connecting glass capillary tube is much less complex than the single stage jet type separator commonly used for gas chromatographic-mass spectrometer coupling. The interface brings no major modification in the design of the mass spectrometer ion source and is totally compatible with the other existing sample introduction system such as gas, solid, and GC inlet. The rapid present progress in system optimization makes it appear that liquid chromatography mass spectrometer provides a highly versatile and powerful analytic system.

For a general study of an unknown mixture, the mass spectrometer scan time is set to be substantially less than the expected widths of the LC peaks (e.g., a scan rate of 10 sec/decade), and mass spectra are collected repetitively during the LC run. The simplest method of LC peak detection is to have the computer display a reconstructed chromatogram of the total ion signal for all peaks of masses above those from the solvent (m/e>160 in FIG. 7). For cases in which the chemical ionization mass spectral behavior of the solvent has not been studied or is not easily predictable, such as in gradient elution, peak detection by visual inspection of the CRT-displayed spectra, either during or after the run may be desirable. In our use to date it has not been necessary to use solute peaks of low mass, although these are often easily discernable in the side-by-side CRT inspection of mass spectra of the effluent, or they can be displayed by computer subtraction of the CI/MS spectrum of the solvent measured from the LC baseline adjacent in the chromatogram.

To illustrate the application, 50 ng of a sample of trilaurin, MW 638, was injected at the head of the LC column, eluted with methanol, and mass spectra were scanned repetitively (20 sec, m/e 70 – 700) on the ~1% of the effluent directed to the MS. The CI spectrum of trilaurin with $CH_3OH$ as the ionizing reagent shows a base peak at m/e 215, in contrast to the 200° isobutane CI spectrum, as well as an order-of-magnitude smaller $(M + H)^+$ peak at m/e 639; the m/e 215 peak presumably is protonated methyl laurate formed by reaction with the solvent ions. A reconstructed liquid chromatogram of masses 160 – 550 indicates a number of eluted components from the supposedly pure sample. A mass chromatogram using m/e 215 clearly shows the trilaurin eluting with a retention time of 17 minutes. The m/e 215 peak eluting at approximately 9 minutes was found to be reproducible, however. This is probably from lauric acid present in the sample as an impurity, although it is possible that some sample saponification occurred in the inlet system.

Figure 7:
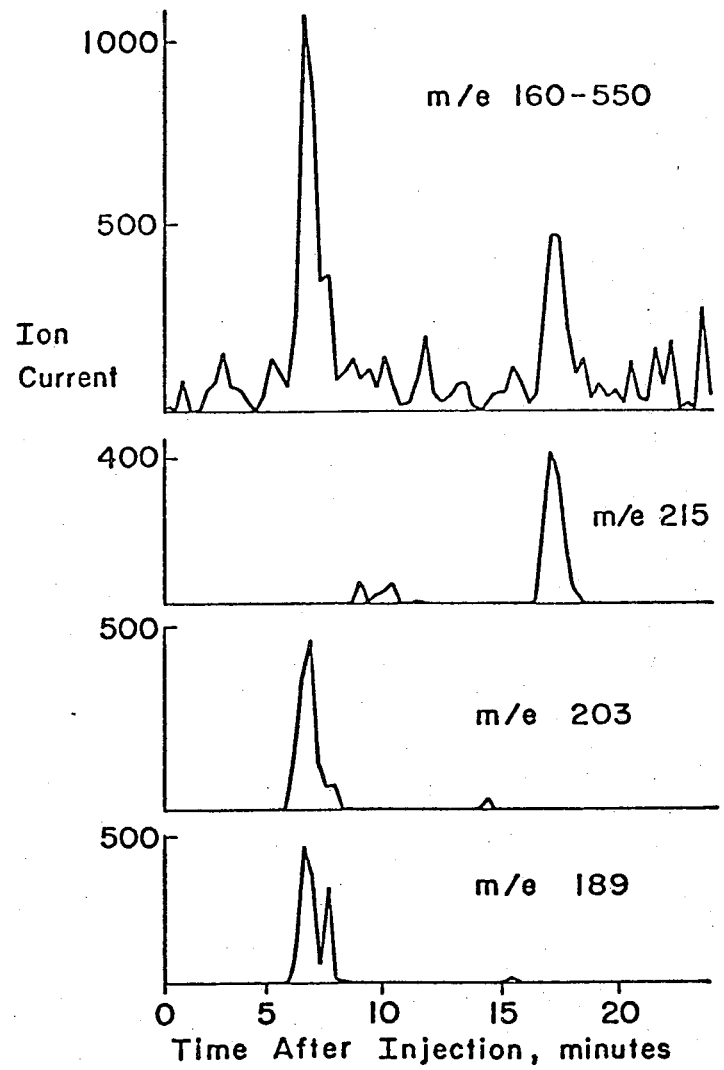
FIG. 7 are mass chromatograms for m/e 189, 203, 215, and the summed ions of m/e 160–550, in arbitrary units of ion current, liquid chromatography separation of 50 × 10⁻⁹g of trilaurin, approximately 1% effluent to mass spectrometer, signal threshold 100 units.

The largest peak in the reconstructed chromatogram was found to arise chiefly from m/e 189 and 203 ions (FIG. 7). These were found even with the injection of pure solvent, and their variability in height with mode of injection indicated that they arise from impurities introduced from the septum. Many of the smaller peaks in the reconstructed chromatogram also appear to be impurities from the inlet system, and scrupulous cleaning is necessary to achieve low noise chromatograms because of the generally high sensitivity of CIMS to all compounds of sufficient volatility. However (FIG. 7), greatly improved noise levels are shown by the individual mass chromatograms; the specificity of these is generally much higher than chromatograms from other detectors, even the multiple wavelength UV spectrometer. Note that if the CIMS information is not sufficient for identification, the eluted sample components indicated in the mass chromatogram can be collected with relative ease because only approximately 1% has been used for CIMS detection, and because of the relatively large solvent volumes involved. Under normal operating conditions, collection of 0.1 ml samples of eluate solutions will give several samples across a single LC peak, and evaporation of these in a sample holder for normal direct probe MS introduction provides sufficient sample for identification from the electron ionization (EI) mass spectrum at the nanogram level.

Figure 8:
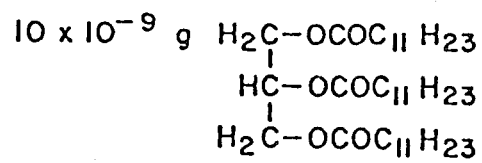
FIG. 8 illustrates single ion detection of m/e 215 for liquid chromatography separation of trilaurin, approximately 1% effluent to the mass spectrometer. "Viscorder" is an analog recording; "4 second averaging" is computer summing of 50 KHz ion signals for 4 second intervals; "integrated" is the running sum of these signals.

For MID mode operation, improvement in sensitivity by monitoring only one or a few particular ions is also possible with the system of the present invention. Injection of 10 ng of trilaurin gives a substantial m/e 215 chromatogram peak using contentional analog recording (FIG. 8), with a substantial improvement in signal/noise with computer summation of the ion signal over 4 sec intervals (note also the presence of the impurity of approximately 9 min retention time). A sample size of 0.5 ng of trilaurin approaches the detection limit (FIG. 8), although the integrated signal clearly shows the presence of the peak. Note that this sensitivity is comparable or superior to that shown by the UV detector for compounds of high molar absorptivities, despite the fact that only 1% of the sample actually entered the mass spectrometer.

In accordance with an alternate embodiment of the invention, micro liquid chromatography columns requiring only about 0.01 ml/minute solvent flow rates are provided, whereby the total effluent could go continuously to the chemical ionization mass spectrometer, so that picogram sensitivities for the liquid chromatography-mass spectrometer system are achieved comparable to those now possible for gas chromatography mass spectrometer systems.

It is apparent that mass spectrometric monitoring of solutes eluted from a liquid chromatograph can be performed simply by directly introducing a small fraction (approximately 1%) of the liquid into the ion chamber of a chemical ionization mass spectrometer. The solvent acts as the ionizing reagent, so that solution flow rates can be orders of magnitude higher than analogous introduction into a normal mass spectrometer. Fragmentation is not extensive in CI spectra, so that these show clear evidence of the molecular weights of the solutes. The LC/MS spectrum depends on both the solvent and the solute, but most of the ions due only to the solutes are usually above the solvent peaks. $(M - H)^+$ is abundant with pentane or hexane as the solvent, $(M + H)^+$ with tetrahydrofuran, acetonitrile, methanol, and water, and $(M + H)^+$ and $(M + CHCl_2)^+$ with chloroform. Sensitivities are high even in comparison to the UV detector, and are generally in the nanogram range.

While in accordance with the Patent Statutes I have illustrated and described the preferred form of the invention, it will be apparent to those skilled in the art that various changes and modifications may be made without deviating from the inventive concepts set forth above.

What is claimed is:

1. In a liquid chromatography-mass spectrometer apparatus for analyzing a solution of a complex mixture, including a liquid chromatography column having an input and an output, pump means connected with said inlet for pumping the solution through said liquid column, mass spectrometer measuring means of the chemical ionization type including an ion source chamber, and interface means for continuously introducing directly into the ion source chamber at least a portion of the eluted effluent produced at the liquid column output; the improvement wherein said interface means comprises a capillary tube the outlet end of which extends into said ion source chamber, said capillary tube outlet end being cylindrical throughout its length and terminating at its extremity in a restriction, thereby to cause the liquid supplied to the ion source chamber to have a relatively low flow rate.

2. Apparatus as defined in claim 1, wherein said chemical ionization mass spectrometer means includes cryogenic pump means connected with said ion source chamber for assisting in the pumping of higher molecular weight solvents.

3. Apparatus as defined in claim 1, wherein said capillary tube has an internal diameter of about 0.076 mm, and wherein the size of the capillary tube restriction is about 1 micron, thereby to permit eluted effluent flow rates on the order of 0.01 ml/minute.

4. Apparatus as defined in claim 1, and further including metering valve means connected with the outlet of the liquid column for regulating the fraction of the eluted effluent from the liquid column that is supplied to said ion chamber source.

5. Apparatus as defined in claim 1, wherein the liquid chromatography column is of the micro-liquid column type having a flow rate on the order of $10^{-2}$ ml/minute, substantially all of the liquid column effluent being supplied continuously to the ion source chamber.

* * * * *

UNITED STATES PATENT AND TRADEMARK OFFICE
Certificate

Patent No. 3,997,298      Patented December 14, 1976

Fred W. McLafferty and Michael A. Baldwin

Application having been made by Fred W. McLafferty and Michael A. Baldwin the inventors named in the patent above-identified, and Cornell Research Foundation, Inc., the assignee, for the issuance of a certificate under the provisions of Title 35, Section 256, of the United States Code, adding the name of Patrick J. Arpino as a joint inventor, and a showing and proof of facts satisfying the requirements of the said section having been submitted, it is this 6th day of Mar., 1984, certified that the name of the said Patrick J. Arpino is hereby added to the said patent as a joint inventor with the said Fred W. McLafferty and Michael A. Baldwin.

Fred W. Sherling,
*Associate Solicitor.*